United States Patent [19]

Braden et al.

[11] 4,137,412

[45] Jan. 30, 1979

[54] PROCESS FOR THE PREPARATION OF SUBSTITUTED CHLOROPYRIMIDINES

[75] Inventors: Rudolf Braden; Kurt Findeisen, both of Odenthal, Germany

[73] Assignee: Bayer Aktiengesellschaft, Leverkusen, Germany

[21] Appl. No.: 860,272

[22] Filed: Dec. 13, 1977

[30] Foreign Application Priority Data

Dec. 31, 1976 [DE] Fed. Rep. of Germany ....... 2659694

[51] Int. Cl.$^2$ .......................................... C07D 239/02
[52] U.S. Cl. ................................................. 544/334
[58] Field of Search ..................... 260/251 R; 544/334

[56] References Cited

U.S. PATENT DOCUMENTS

| | | | |
|---|---|---|---|
| 3,682,916 | 8/1972 | Findeisen et al. | 260;544/251 R;334 |
| 3,920,649 | 11/1973 | Beck et al. | 544/334 |
| 4,026,892 | 5/1977 | Beck et al. | 544/334 |

*Primary Examiner*—Nicholas S. Rizzo
*Attorney, Agent, or Firm*—Sprung, Felfe, Horn, Lynch & Kramer

[57] ABSTRACT

A process for the preparation of a chlorinated pyrimidine, chloroalkyl-substituted in the 5-position of the general formula

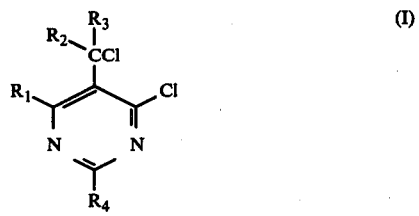

wherein
$R_1$ represents fluorine, chlorine, bromine, trichloromethyl, phenyl or hydrogen or a second chlorinated pyrimidine ring substituted in the 5-position,
$R_2$ represents hydrogen, fluorine, chlorine, bromine, alkyl with 1 to 6 C-atoms, phenyl, nitrophenyl or chlorophenyl,
$R_3$ represents hydrogen, fluorine, bromine or chlorine and
$R_4$ represents fluorine, chlorine, bromine, trichloromethyl or hydrogen; which comprises contacting a halogeno-azaalkene of the formula

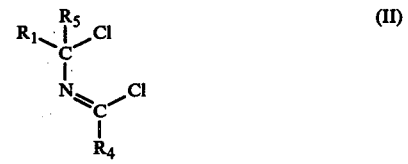

wherein
$R_1$ represents fluorine, chlorine, bromine, trichloromethyl, phenyl, hydrogen or —CCl$_2$—N=CCl$_2$;
$R_4$ represents fluorine, chlorine, bromine of trichloromethyl; and
$R_5$ represents fluorine, chlorine, bromine or hydrogen with an α, β-unsaturated nitrile of the formula

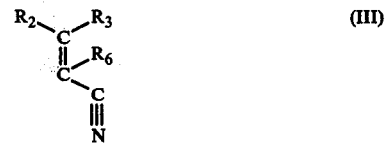

wherein
$R_2$ represents hydrogen, chlorine, fluorine, alkyl with 1 to 6 carbon atoms, cycloalkyl, phenyl, nitrophenyl or chlorophenyl;
$R_3$ represents hydrogen, fluorine or chlorine, and
$R_6$ represents hydrogen, fluorine, chlorine or bromine.

13 Claims, No Drawings

PROCESS FOR THE PREPARATION OF SUBSTITUTED CHLOROPYRIMIDINES

BACKGROUND OF THE INVENTION

1. Field of the Invention

The invention relates to a process for the preparation of chlorinated pyrimidines, chloro alkyl-substituted in the 5-position, of the general formula

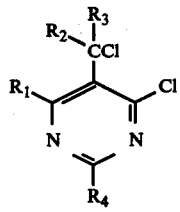

wherein $R_1$ represents fluorine, chlorine, bromine, trichloromethyl, phenyl or hydrogen or a second chlorinated pyrimidine ring substituted in the 5-position, $R_2$ represents hydrogen, fluorine, chlorine, bromine, alkyl with 1 to 6 C atoms, phenyl, nitrophenyl or chlorophenyl, $R_3$ represents hydrogen, fluorine, bromine or chlorine and $R_4$ represents fluorine, chlorine, bromine, trichloromethyl or hydrogen.

2. Discussion of Prior Art

It is already known that chlorinated pyrimidines can be prepared by reacting acetonitriles with chlorinated isocyanide dichlorides (DT-OS (German Published Specification) No. 1,670,854). In order to be able to prepare chlorinated pyrimidines with a chlorine-containing alkyl group in the 5-position of the pyrimidine ring by this process, it is necessary to use propionitriles which have a chlorine atom in the β-position and are unsubstituted in the α-position as the starting materials. In most cases, the β-chloropropionitriles required as the starting material must be prepared from the α,β-unsaturated nitriles. Thus, β-chloropropionitrile is prepared from acrylonitrile, but undesired by-products are formed.

According to the present invention there is provided a process for the preparation of the chlorinated pyrimidines, chloro-alkyl substituted in the 5-position, of the formula I, in which halogeno-azaalkenes of the general formula II

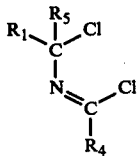

wherein $R_1$ can represent fluorine, chlorine, bromine, trichloromethyl, phenyl, hydrogen or —CCl$_2$—N=CCl$_2$, $R_4$ can represent fluorine, chlorine, bromine or trichloromethyl and $R_5$ can represent fluorine, chlorine, bromine or hydrogen, are reacted with α,β-unsaturated nitriles of the general formula III

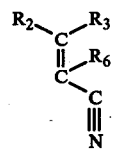

wherein $R_2$ represents hydrogen, chlorine, fluorine, alkyl with 1 to 6 C atoms, cycloalkyl, phenyl, nitrophenyl or chlorophenol, $R_3$ represents hydrogen, fluorine or chlorine and $R_6$ represents hydrogen, fluorine, chlorine or bromine.

The starting components (II) and (III) are reacted with one another in accordance with the process according to the invention in approximately stoichiometric proportions or with an excess of one or other of the components. If a bis-(isocyanide dihalide) is employed as the starting component (II), the nitrile component is employed in approximately twice the stoichiometric proportion.

Compounds of the formula (II) which are suitable for the process are, for example, chloromethyl isocyanide dichloride, trichloromethyl isocyanide dichloride, pentachloroethyl isocyanide dichloride, pentachloroethyl isocyanide dichloride, phenyl-dichloromethyl isocyanide dichloride and perchloro-2,5-diazahexa-1,5-diene; perchloro-3,6-diazaocta-2,6-diene; and 1,1,3,4,4,4-hexachloro-2-azabut-1-ene and fluoro-dichloromethyl isocyanide dichloride.

Unsaturated nitriles of the formula (III) which are suitable for the process are, for example, acrylonitrile, methacrylonitrile, crotononitrile, cinnamic acid nitrile, 3-nitrocinnamic acid nitrile, 3-chlorocinnamic acid nitrile, α-chloroacrylonitrile, α,β-dichloroacrylonitrile, trichloroacrylonitrile, fumaric acid nitrile and α-bromoacrylonitrile.

The process according to the invention can be carried out in the presence or absence of inert solvents or diluents at temperatures from 20°–350° C. The reaction is preferably carried out at 100°–220° C.

The reaction can be carried out under normal pressure and under autogenous pressure and optionally in the gas phase, preferably a pressure up to 20 atm is suitable.

In general, it is advantageous in the process according to the invention to heat the starting components together in stoichiometric amounts or to use one of the starting components or the end product as a solvent. It can be advantageous to initially heat the component used as a solvent to the reaction temperature and then to introduce the second component.

Aliphatic, cycloaliphatic and aromatic hydrocarbons with up to 10 C atoms can be used as the solvent, it being possible for the hydrocarbons mentioned to be optionally substituted by halogens and/or nitro groups. Examples which may be mentioned are: methylene chloride, chloroform, carbon tetrachloride, dichloroethane, trichloroethane, trichloroethylene, 1,2-dichloropropane, trichloropropane, sulpholane, chlorobenzene, dichlorobenzene, nitrobenzene or one of the reactants in excess. Preferred solvents are chlorinated hydrocarbons or sulphones.

The reaction can be accelerated by acid or basic catalysts. The catalysts can be applied to an inert support material. Suitable acid catalysts are, for example, Lewis acids, such as iron-III chloride, aluminium chloride, zinc chloride, copper-I chloride, palladium chloride, boron trifluoride, antimony trichloride and titanium tetrachloride. Examples of suitable basic catalysts which may be mentioned are: triethylamine, pyridine and dimethylformamide.

The catalysts are generally added in an amount of 0.001 to 10% by weight of one of the starting components, or the components are passed over the catalyst, which has been applied to a solid support. A catalyst amount of 0.1 to 5% by weight has proved particularly advantageous.

The reaction can be illustrated with the aid of the following equation:

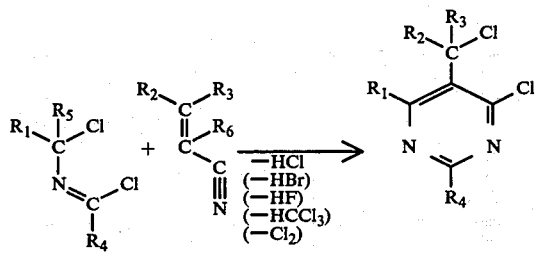

Preferred processes according to the present invention comprise reacting acrylonitrile with a perchlorinated alkyl isocyanide dichloride.

According to a particularly preferred embodiment, trichloromethyl isocyanide dichloride is reacted with acrylonitrile, preferably in the temperature range from 100° to 350° C., in the presence of catalytic amounts of a Lewis acid catalyst, 2,4,6-trichloro-5-chloromethyl-pyrimidine being obtained in very good yields.

The process according to the invention is therefore particularly suitable for the preparation of chlorinated pyrimidines carrying a substituted methyl group in the 5-position, in particular 2,4,6-trichloro-5-chloromethyl-pyrimidine. In this respect, the course of the reaction is surprising since in general cyclisation reactions with $\alpha,\beta$-unsaturated nitriles take place with the inclusion of the $\beta$-C atom in the ring formed.

2,4,6-Trichloro-5-chloromethylpyrimidine is a known intermediate product. The volume of the products of the process are new intermediate products which are suitable, for example, for the preparation of reactive dyestuffs. Compounds of formula (I), except those in which $R_1$, $R_3$ and $R_4$ denote chlorine and $R_2$ denotes methyl, thus also form part of the present invention.

The Examples given are intended to illustrate the process according to the invention in more detail, without, however, limiting it to these.

EXAMPLE 1

600 g (2.78 mols) of trichloromethyl isocyanide dichloride are heated to 170° C. in a 1 l stirred flask with a reflux condenser and dropping funnel. 112 g (2.11 mols) of acrylonitrile, in which 10 g of $FeCl_3$ are dissolved, are added dropwise in the course of 1 hour. During this addition, the temperature is kept in the range from 160° to 175° C. The mixture is then heated to 185° C. for a further 30 minutes. During this, boiling under reflux stops. The reaction mixture is distilled. This gives:

1. 165 g     up to boiling point$_{15}$ 100° C
this fraction contains 92% of trichloromethyl isocyanide dichloride
2. 412.2 g     boiling point$_{15}$ 145 – 147° C
3. 50.0 g of residue The 2nd fraction contains 99.2% of 2,4,6-trichloro-5-chloromethylpyrimidine of molecular weight 232; melting point 110° C.; yeild 84% of theory. The IR spectrum is identical to the spectrum of a sample prepared according to the process of DT-OS (German Published Specification) No. 1,670,854, Example 6.

EXAMPLE 2

70 g of trichloromethyl isocyanide dichloride are heated to 165° C. in a stirred flask and 26 g of cinammic acid nitrile and 1 g of sublimed $FeCl_3$ are added in the course of 1 hour. The reaction product is distilled. This gives 1. 36 g of first runnings    up to boiling point$_{15}$ 70° C
consisting of 89.9% of trichloromethyl isocyanide dichloride and cinammic acid nitrile
2. 28.4 g     boiling point$_{0.5}$ 95 – 170° C
3. 10.6 g of residue The 2nd fraction consists of 2,4,6-trichloro-5-phenyl-chloromethylpyrimidine to the extent of 60.6% and of cinammic acid nitrile to the extent of 25.3%. On renewed distillation, the 2nd fraction gives pure 2,4,6-trichloro-5-phenylchloromethylpyrimidine. Boiling point$_{0.3}$ 175°; melting point 58° C., molecular weight 308.

The NMR spectrum shows a signal for a single proton at 6.8 ppm and a signal for five protons at 7.3 ppm. The starting nitrile was converted to the extent of 69.5%. The yield, relative to converted cinammic acid nitrile, was 43%.

EXAMPLE 3

300 g of trichloromethyl isocyanide dichloride are heated to 168° C. in a stirred flask. A mixture of 92 g of $\alpha$-chloroacrylonitrile and 5 g of $FeCl_3$ is added dropwise in the course of 2 hours. During this addition, the temperature is kept in the range from 163°–168° C. The temperature is then increased to 180° C. in the course of one hour.

The following are obtained from the reaction mixture by distillation:
1. 159.4 g, boiling point$_{15}$ 50°–100° C.
This fraction contains 135 g of trichloromethyl isocyanide dichloride.
2. 173.8 g, boiling point$_{15}$ 140°–150° C.
This fraction solidifies. Melting point 98°–102° C.
3. 35.0 g of a resinous residue.
Fraction 2) consists of 2,4,6-trichloro-5-chloromethyl-pyrimidine to the extent of 82.4%, as was demonstrated by gas chromatography and by comparison of the IR spectra.

EXAMPLE 4

2,4-Dichloro-5-chloromethyl-6-trichloromethylpyrimidine

A solution of 1 g of $FeCl_3$ in 11.0 g (0.21 mol) of acrylonitrile is added to 70 g (0.2345 mol) of penta-chloroethyl isocyanide dichloride at 180° C. in the course of 30 minutes. During this addition, the mixture is cooled in order to keep the exothermic reaction, which starts immediately, at 170°–180° C.

The reaction mixture is distilled in vacuo. This gives, in addition to 26.8 g of recovered pentachloroethyl isocyanide dichloride, which still contains 3.3 g of perchloro-2-aza-buta-1,4-diene, boiling point$_{15}$ 95°–140° C., 32.7 g of 2,4-dichloro-5-chloromethyl-6-trichloromethyl-pyrimidine, boiling point$_{0.3}$ 135° C., n$_D^{20}$: 1.5892, purity 96%.

What is claimed is:

1. A process for the preparation of a chlorinated pyrimidine, chloroalkyl-substituted in the 5-position of the formula

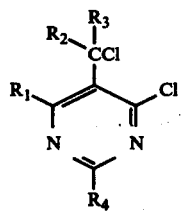
(I)

wherein $R_1$ represents fluorine, chlorine, bromine, trichloromethyl, phenyl or hydrogen or a second chlorinated pyrimidine ring substituted in the 5-position, $R_2$ represents hydrogen, fluorine, chlorine, bromine, alkyl with 1 to 6 C atoms, phenyl, nitrophenyl or chlorophenyl, $R_3$ represents hydrogen, fluorine, bromine or chlorine and $R_4$ represents fluorine, chlorine, bromine, trichloromethyl or hydrogen, which comprises contacting a halogeno-azaalkene of the formula

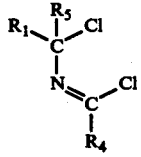
(II)

wherein $R_1$ represents fluorine, chlorine, bromine, trichloromethyl, phenyl, hydrogen or —CCl$_2$—N=CCl$_2$;

$R_4$ represents fluorine, chlorine, bromine or trichloromethyl; and $R_5$ represents fluorine, chlorine, bromine or hydrogen with an α,β-unsaturated nitrile of the formula

(III)

wherein $R_2$ represents hydrogen, chlorine, fluorine, alkyl with 1 to 6 carbon atoms, cycloalkyl, phenyl, nitrophenyl or chlorophenyl;

$R_3$ represents hydrogen, fluorine or chlorine, and $R_6$ represents hydrogen, fluorine, chlorine or bromine.

2. A process according to claim 1 wherein the reaction is carried out in the presence of inert solvent.

3. A process according to claim 2 wherein the inert solvent is a chlorinated hydrocarbon or sulfone.

4. A process according to claim 1 wherein the reaction is carried out at a temperature of from about 20° to 350° C.

5. A process according to claim 4 wherein the process is carried out in the presence of a catalyst.

6. A process according to claim 5 wherein said catalyst is a metal halide.

7. A process according to claim 5 wherein said catalyst is a Lewis acid.

8. A process according to claim 1 wherein one of the starting reactants is employed in a stoichiometric excess.

9. A process according to claim 1 wherein acrylonitrile is reacted with a perchlorinated alkyl isocyanide dichloride.

10. A process according to claim 1 wherein trichloromethyl isocyanide dichloride is reacted with acrylonitrile in the presence of a Lewis acid catalyst.

11. A process according to claim 1 carried out wherein the reaction is carried out at atmospheric pressure.

12. A process according to claim 1 wherein the reaction is carried out at autogenous pressure.

13. A process according to claim 1 wherein the reaction is carried out at a temperature of from about 20° to 350° C. in the presence of an acid or basic catalyst.

* * * * *